United States Patent [19]

Wetzel et al.

[11] 4,294,996
[45] Oct. 13, 1981

[54] METHOD OF REDUCING FORMATION OF CHLORINATED DIOXINS IN MANUFACTURE OF CHLORINATED PHENOLS

[75] Inventors: William H. Wetzel, Federal Way; Hsi-Lung Pan, Seattle; Robert J. Goodwin, Puyalup; John E. Wilkinson, Gig Harbor, all of Wash.

[73] Assignee: Reichhold Chemicals, Incorporated, White Plains, N.Y.

[21] Appl. No.: 157,447

[22] Filed: Jun. 9, 1980

[51] Int. Cl.³ .................. C07C 39/36; C07C 39/27
[52] U.S. Cl. .................... 568/776; 568/755; 568/779
[58] Field of Search ............... 568/776, 755, 779

[56] References Cited

U.S. PATENT DOCUMENTS

| | | | |
|---|---|---|---|
| 3,760,010 | 9/1973 | Widiger | 568/755 |
| 3,816,268 | 6/1974 | Watson et al. | 203/38 |
| 3,909,365 | 7/1979 | Christena | 203/38 |
| 4,016,047 | 4/1977 | Christena | 568/755 |
| 4,160,114 | 7/1979 | Shelton et al. | 568/776 |
| 4,228,309 | 10/1980 | Hatcher | 568/755 |

*Primary Examiner*—Werren B. Lone

[57] ABSTRACT

The invention covers the use of novel co-catalysts as inhibitors that reduce the formation of undesirable chlorinated dioxins during the preparation of pentachlorophenol and tetrachlorophenol from phenol or lower chlorinated phenols.

15 Claims, No Drawings

METHOD OF REDUCING FORMATION OF CHLORINATED DIOXINS IN MANUFACTURE OF CHLORINATED PHENOLS

BACKGROUND OF THE INVENTION

This invention relates to the use of novel co-catalysts which produce a reduction in the formation of undesirable chlorinated dioxin by-products in the preparation of pentachlorophenol or tetrachlorophenol from phenol or lower chlorinated phenols.

In processes well-known in the art for the chlorination of phenols or partially chlorinated phenols such as pentachlorophenol, the usual practice has been to use such catalysts as aluminum chloride, aluminum, antimony pentachloride and ferric chloride. Subsequent to chlorination, the molten tetrachlorophenol or pentachlorophenol is pumped to heated storage facilities pending flaking, prilling or molding operations which are necessary to change the material to a commercially usable form as finished product. In the case of pentachlorophenol, valuable for its fungicidal activity, the specifications are low alkali insoluble content, low insolubles in alkane solvents and a minimum of 86% pentachlorophenol content.

Prior art relating to the lowering of the amount of undesirable chlorinated dioxins formed in the preparation of pentachlorophenol is U.S. Pat. No. 4,160,114 to Shelton et al, wherein organic sulfides are directly utilized as a co-catalyst along with aluminum chloride to effect this result. The specification of the Shelton et al patent is incorporated by way of reference in this application.

There also exists prior art taught in U.S. Pat. Nos. 3,816,268 and 3,909,364 wherein chlorinated dioxins in pentachlorophenol are elaborately reduced to a lower level by distillation under vacuum using stabilizers to prevent decomposition at the required high temperatures. Although low amounts of dioxins are obtained in the distilled pentachlorophenol, a residue of pot material remains containing extremely high quantities of dioxins.

Undesirable by-products called chlorinated dioxins are present in amounts of from 200 to 8,000 parts per million in pentachlorophenol and in lesser amounts of tetrachlorophenol as manufactured by the classical phenol chlorination methods. The primary undesirable dioxins formed are hexachlorodibenzodioxins, heptachlorodibenzodioxins and octachlorodibenzodioxins.

It has been found that the amount of these chlorinated dioxins in tetrachlorophenol or pentachlorophenol can be reduced by the use of certain elements and compounds formed from these elements which, when used in conjunction with aluminum chlorination catalysts involved in synthesis, were effective in inhibiting the amount of chlorinated dioxins formed. Furthermore, these elements or compounds containing these elements acting as inhibitors for the formation of dioxins can be utilized within existing pentachlorophenol plant systems and equipment without modification or need for new construction. These inhibiting elements in low amounts can be placed within the reaction vessel along with the usual aluminum chlorination catalyst to effect reduction of chlorinated dioxins with little noticeable loss in manufacturing time and with little effort. The co-catalyst-inhibitors are also effective during holding cycles necessary in the manufacturing process. The significantly low amount of chlorinated dioxins produced during the practice of this invention exists only in the highly dispersed or diluted form in the finished product. This reaction in dioxins eliminates the necessity of disposing of highly concentrated dioxins in pot residue that arise from the distillation procedure in prior art, as well as presenting a product that has a substantially reduced dioxin content.

It has been found that certain elements have dioxin-reducing properties and can be utilized either directly in their elemental form or in halogenated or sulfonated form, or as alkyl oxides and mixtures of elements, and such compounds or elements effect the reduction of dioxins in tetrachlorophenol or pentachlorophenol produced by the standard commercial chlorination process.

Exemplary of the elements and compounds formed therefrom found to have appreciable dioxin reduction properties during the chlorination of phenols using known chlorination catalyst are antimony, bismuth, chromium, cobalt, gadolinium, germanium, iridium, magnesium, manganese, niobium, rhenium, rhodium, samarium, zirconium and tin, and the halides, sulfides and lower alkyl oxides formed from these elements or mixturs thereof. These elements or compounds formed therefrom act as co-catalyst inhibitors with the standard known catalyst used in commercial chlorination processes to produce polychlorinated phenols by reducing significantly the formation of chlorinated dioxins which are undesirable by-products.

Typical of the catalysts used in production of chlorinated phenols and with which the co-catalyst inhibitors of this invention have been found to produce excellent chlorinated dioxin reduction results are aluminum chloride, ferric chloride, aluminum tris-butoxide, antimony chloride, stanous chloride and metallic alumina, antimony, copper, tin and mixtures thereof.

It has also been found that the presence of from about 0.0001/moles to about 0.05 moles per mole of phenol or lower chlorinated phenol of a sulfur-containing co-catalyst produces excellent results in the system using the inhibitors of this invention. Typical sulfur-bearing compounds that can be used include sulfur, diphenyl sulfide, diphenyl disulfide, dicresyl disulfide, dihexadecyl sulfide and dibenzothiophenol thiophenol, para-chlorothiophenol, para, paradichlorophenyl sulfide, sodium hydrosulfide, 2,2'-thio bis (4,6-dichlorophenol) benzyl disulfide, diisopentyl sulfide, naphthalenethiol, heptyl sulfide and hexachlorophenyl sulfide.

In the manufacture of tetrachlorophenol or pentachlorophenol, the preferable quantity of the co-catalyst inhibitors to be added with the catalyst is from about 0.0001 to about 0.03 moles per mole of phenol or chlorophenol starting materials although it has been found that the use of 0.0001 to 0.5 moles of these inhibitors will produce dioxin-reducing results.

It was found that the novel co-catalyst inhibitors of this invention, when added with aluminum chloride of metallic aluminum catalysts in a phenol chlorination process, produced a pronounced reduction of chlorinated dioxins with reduction in the range of about 4% to about 26%. The following chlorinated dioxin inhibitors and mixtures thereof produced such significant reduction in total chlorinated dioxins:
Antimony pentachloride
Chromium dichloride
Chromium powder
Chromium sulfide
Cobalt metal Gadolinium trichloride
Germanium tetrachloride
Hafnium tetrachloride
Indium chloride
Magnesium turnings
Manganese dichloride
Niobium chloride
Zirconium tetrachloride and the following chlorinated dioxin inhibitors produced significant reduction in the more toxic hexachlorodioxins with a reduction of from about 40% to 75%:

Antimony pentachloride
Antimony powder
Bismuth trichloride
Chromium metal
Cobalt fluoride
Cobalt metal
Hafnium tetrachloride
Iridium chloride
Niobium pentachloride
Rhenium pentachloride
Rhodium chloride
Rubidium trichloride
Samarium trichloride
Tantalum chloride
Tin powder
Tungsten hexachloride
Zinc fluoride
Zirconium tetrachloride While most of the co-catalyst-inhibitors are effective when used with an aluminum chloride catalyst, it has been found that zirconium tetrachloride and/or hafnium tetrachloride can be used as the sole catalyst with the result that chlorinated dioxins are reduced in the chlorinated phenol process.

The practice of this invention is further illustrated by the following examples. It is not intended, however, that this invention be limited by or to the examples.

EXAMPLE I

A series of runs was made against controls to determine the reduction in chlorinated dioxins. The procedure for preparing pentachlorophenol from a predominantly monochlorophenol feedstock was accomplished in the following manner:

A one-kilogram sample of the feedstock plus 0.1 g of diphenylsulfide promoter were loaded into a 2,000 ml glass reactor equipped with a stirrer, heating mantle, cooling system, a thermometer, a sintered glass chlorine diffuser and an exit line for hydrochloric acid vapor. The mixture was heated to a temperature of 125° C. and chlorine gas was sparged in at 510 g/hr. During the chlorination, the chlorine feed rate was reduced stepwise to 120 g/hr so that bypassing was minimized. After two hours 0.57 g of aluminum powder or an equivalent amount of aluminum chloride was added followed by the requisite amount of the co-catalyst inhibitor. The batch temperature was held at 125° C. by water cooling until the freezing point reached 115° C.; thereafter, the batch temperature was allowed to rise so that it stayed about 10° C. above the freezing point of the reaction mixture. When the freezing point reached 178° C. to 180° C. the chlorination was stopped. Samples of the product were taken for analysis.

The results of a series of thirty runs that were made illustrate the significant reduction in undesirable dioxins obtained by the use of the inhibitors in this invention, when compared with the control runs.

In the preparation of the pentachlorophenol, various elements and halides and sulfides of the elements were used as the inhibitors, and tested against a control to determine the percent of total reduction of chlorinated dioxins. In the control runs, no co-catalyst-inhibitors were used.

The results of these tests are set forth in Table I.

EXAMPLE II

A second series of fifteen runs was made, which show the effects of varying levels of the inhibitors on reduction of chlorinated dioxin. The results of these fifteen runs are set forth in Table II which demonstrates the ranges of the amounts of inhibitors that can be used.

The following footnotes for Tables I and II show (a) the method of testing for the alkali insolubles, (b) total chlorinated phenols (TCP), and (c) the analysis of chlorinated dioxin in parts per million (PPM).

[a]The alkali-insoluble material in pentachlorophenol is determined in the following way: Dissolve a 1-gram sample in 50 milliliters of N/1 NaOH and 50 milliliters of distilled water, warming to about 60° C. and crushing larger particles with flattened glass rod. Filter through a tared Gooch crucible with an asbestos mat, wash free from alkali with distilled water and dry at 100° C. to constant weight. The increase in weight represents alkali insoluble matter. It is expressed mathematically as follows:

$$\frac{\text{Grams residue} \times 100}{\text{Grams of Sample}} = \text{percent alkali insolubles}$$

[b]The total chlorinated phenols are determined in the following way: The total chlorinated phenol content is determined by titration of dry pentachlorophenol with sodium hydroxide.

Reagents (a) $CO_2$-free 95 percent ethyl alcohol.
Note: Ethyl alcohol denaturated according to formula 2B of the appendix to Regulations No. 3, Formulae for Completely and Specially Denatured Alcohol is suitable for this purpose. Distill the ethyl alcohol (formula 2B) over caustic pellets. Store in a stoppered bottle.
(b) Meta cresol purple indicator solution. Place 0.100 grams of meta cresol purple in a small mortar, add 2.62 milliliters of N/10 aqueous NaOH. Rub with the pestle until solution is complete. Transfer the solution to a 100-milliliter volumetric flask and make up to volume with distilled water.

Procedure

Weigh a 1.0000-gram sample and transfer to a clean 250-milliliter Erlenmeyer flask. Add 65 milliliters of ethyl alcohol and gently swirl until solution of the sample is complete. Add 35 milliliters of distilled water and subtract from above titration. Net ml. of N/10 NaOH×0.02663×100=Total chlorinated phenols as percent pentachlorophenol.
Note: Ethyl alcohol solutions pick up $CO_2$ from the air fairly rapidly, therefore, titrate sample immediately after dissolving in the alcohol.

$^c$All chlorodioxin analyses performed on these samples were accomplished via high pressure liquid chromatography (HPLC). Non-polar components were first isolated from the sample matrix using two passes through two alumina columns using benzene for the former and 2% methylene chloride in hexane (v/v) for the latter. The eluant was then analyzed via HPLC and quantitated for the individual chlorodibenzo-p-dioxin components.

Although the invention is described in detail for the purposes of illustration, it is to be understood that such detail is solely for that purpose and that variations can be made therein by those skilled in the art without departing from the spirit and scope of the invention except as it may be limited by the claims.

| | EFFECT OF INHIBITORS FOR REDUCTION OF CHLORINATED DIOXINS IN PENTACHLOROPHENOL SYNTHESIS | | | | | | | | | | | |
|---|---|---|---|---|---|---|---|---|---|---|---|---|
| | DIOXIN INHIBITOR | | PROPERTIES OF PCP PRODUCT | | | | ANALYSIS OF CHLORINATED DIOXINS, PPM[c] | | | | | % REDUCTION |
| EXPERIMENT NO. | NAME | AMT., ATOMS OR MOLES | FREEZE POINT, °C. | CAUSTIC INSOLUBLE,[a] % | T.C.P.,[b] % | HEXA | HEPTA | OCTA | TOTAL | | | TOTAL DIOXINS |
| 1 | Antimony Pentachloride (SbCl$_5$) | 0.0033 | 180 | 0.50 | 95.7 | 22 | 180 | 647 | 850 | | | 26.2 |
| 2 | Control for Above Experiment | 0.0 | 180 | 0.65 | 97.7 | 90 | 207 | 853 | 1150 | | | 0.0 |
| 3 | Bismuth Chloride (BiCl$_3$) | 0.0063 | 178 | 0.09 | 100 | 2.5 | 96.5 | 445.5 | 544.5 | | | 65.2 |
| 4 | Bismuth Chloride (BiCl$_3$) | 0.0095 | 178 | 0.30 | 96.8 | 12.6 | 281 | 804 | 1098 | | | 30.0 |
| 5 | Bismuth Chloride and Tin (BiCl$_3$/Sn) | 0.0063/ 0.025 | 178 | 0.05 | 96.2 | 12.6 | 164 | 811 | 988 | | | 36.9 |
| 6 | Bismuth Chloride and Chromium (BiCl$_3$/Cr) | 0.0063/ 0.01 | 178 | 0.03 | 97.8 | 10.1 | 138 | 552 | 700 | | | 55.3 |
| 7 | Chromium Metal (Cr) | 0.021 | 178 | 0.10 | 98.1 | 5.1 | 64 | 452 | 502 | | | 68.0 |
| 8 | Chromium Sulfide (Cr$_2$S$_3$) | 0.0126 | 178 | 0.33 | 96.7 | 5.1 | 120 | 638 | 763 | | | 51.2 |
| 9 | Control for Avove Experiments | 0.0 | 180.5 | 0.20 | 97.6 | 5.1 | 111 | 1450 | 1566 | | | 0.0 |
| 10 | Chromium Dichloride (CrCl$_2$) | 0.0063 | 180.5 | 0.4 | 97.6 | 25 | 148 | 643 | 816 | | | 7.0 |
| 11 | Cobalt Metal (Co) | 0.017 | 180.5 | 0.23 | 97.5 | 6 | 91 | 736 | 832 | | | 5.1 |
| 12 | Control for Above Experiments | 0.0 | 180.5 | 0.23 | 95.6 | 21 | 136 | 720 | 877 | | | 0.0 |
| 13 | Cobalt Fluoride (CoF$_3$) | 0.042 | 179.5 | 0.75 | 94.9 | 24 | 225 | 756 | 1036 | | | 10 |
| 14 | Control for Above Experiment | 0.0 | 180 | 0.65 | 97.7 | 90 | 207 | 853 | 1150 | | | 0.0 |
| 15 | Gadolinium Chloride (GdCl$_3$) | 0.0063 | 179 | 0.33 | 97.8 | 5 | 117.0 | 611.7 | 734 | | | 18.9 |
| 16 | Control for Above Experiment | 0.0 | 179 | 0.18 | 97.07 | 4 | 140 | 760 | 905 | | | 0.0 |
| 17 | Germanium Chloride (GeCl$_4$) | 0.0063 | 178 | 0.05 | 97.7 | 15 | 158 | 642 | 815 | | | 12 |
| 18 | Iridium Chloride (IrCl$_3$) | 0.0033 | 178 | 0.10 | 98 | 13 | 88 | 312 | 413 | | | 55.4 |
| 19 | Indium Chloride (InCl) | 0.0063 | 179.5 | 0.03 | 98.5 | 10 | 82 | 705 | 797 | | | 14 |
| 20 | Control for Above Experiment | 0.0 | 178.5 | .04 | 97.9 | 13 | 120 | 794 | 927 | | | 0.0 |
| 21 | Magnesium Metal (Mg) | 0.021 | 180 | 0.30 | 96.7 | 99 | 181 | 703 | 984 | | | 14.5 |
| 22 | Control for Above Experiment | 0.0 | 180 | 0.65 | 97.7 | 90 | 207 | 853 | 1150 | | | 0.0 |
| 23 | Manganese Dichloride (MnCl$_2$) | 0.0063 | 181 | 0.20 | 98.3 | 3 | 41 | 485 | 529 | | | 19 |
| 24 | Control for Above Experiment | 0.0 | 179 | 0.18 | 98 | 4 | 150 | 809 | 962 | | | 0.0 |
| 25 | Rhenium Pentachloride ReCl$_5$) | 0.0015 | 178 | 0.13 | 99.4 | 8 | 53 | 479 | 539 | | | 42 |
| 26 | Rhodium Chloride (RhCl$_3$) | 0.0038 | 178 | 0.08 | 97.7 | 15 | 117 | 499 | 631 | | | 32 |
| 27 | Samarium Chloride (SmCl$_3$) | 0.0063 | 180 | 0.48 | 98.4 | 10 | 76 | 246 | 332 | | | 64.2 |
| 28 | Control for Above Experiments | 0.0 | 178.5 | 0.035 | 97.9 | 13 | 120 | 795 | 927 | | | 0.0 |
| 29 | Tin (Sn) | 0.025 | 178.5 | 0.06 | 97.2 | 8 | 108 | 585 | 701 | | | 42.5 |
| 30 | Control for Above Experiment | 0.0 | 180.5 | 0.20 | 97.6 | 5 | 111 | 1450 | 1566 | | | 0.0 |

TABLE II

EFFECT OF VARYING LEVELS OF INHIBITORS ON DIOXIN REDUCTION

| Example No. | Co-Catalyst (atoms or moles) | Freezing Point, °C. | Caustic Insols., %[a] | T.C.P.,[b] % | Dioxins ppm[c] | | | | % Reduction Dioxins |
|---|---|---|---|---|---|---|---|---|---|
| | | | | | Hexa | Hepta | Octa | Total | |
| 1 | None | 180 | 0.81 | 99.2 | 18 | 207 | 4377 | 4601 | Control |
| 2 | Tin Powder (0.0021) | 178.5 | 0.83 | 97.0 | 18 | 249 | 3482 | 3749 | 18.5 |
| 3 | Tin Powder (0.21) | 178 | 0.05 | 99.4 | 18 | 217 | 706 | 941 | 79.5 |
| 4 | Chromium Powder (0.0021) | 178 | 0.17 | 97.6 | 18 | 280 | 1529 | 1827 | 60.3 |
| 5 | Chromium Powder (0.21) | 178 | 0.44 | 99.6 | 107 | 663 | 3529 | 4299 | 6.6 |
| 6 | Antimony Powder (0.0021) | 178 | 0.04 | 99.4 | 13 | 217 | 1118 | 1349 | 70.7 |
| 7 | Antimony Powder (0.21) | 178 | 0.00 | 100.5 | 13 | 202 | 1059 | 1274 | 72.3 |
| 8 | Niobium Pentachloride (0.0021) | 177.5 | 0.05 | 99.4 | 13 | 135 | 588 | 736 | 84.0 |
| 9 | Niobium Pentachloride (0.21) | 178 | 1.12 | 98.7 | 72 | 193 | 1686 | 1951 | 57.6 |
| 10 | Bismuth Trichloride (0.0021) | 178 | 0.03 | 98.8 | 18 | 155 | 1224 | 1397 | 69.6 |
| 11 | Bismuth Trichloride (0.21) | 178 | 1.63 | 97.4 | 12 | 262 | 957 | 1231 | 73.2 |
| 12 | Manganese Dichloride (0.0021) | 178 | 0.20 | 98.3 | 12 | 55 | 518 | 585 | 87.3 |
| 13 | Manganese Dichloride (0.21) | 178.5 | 0.84 | 100.5 | 18 | 311 | 1565 | 1893 | 58.9 |
| 14 | Zirconium Tetrachloride (0.0021) | 178 | 0.05 | 98.1 | 15 | 176 | 790 | 981 | 78.7 |
| 15 | Zirconium Tetrachloride (0.21) | 178 | 2.28 | 98.6 | 30 | 580 | 2761 | 3370 | 26.8 |

We claim:

1. A process for producing polychlorinated phenols having reduced amount of chlorinated dioxin formed therein during processing comprising reacting at a temperature of from 10° C. to 190° C. (A) a phenol, which is at least one member selected from a group consisting of phenol and lower chlorophenols and mixtures thereof, (B) chlorine to form a reaction mixture in the presence of from about 0.005 to about 0.016 moles per mole of (A) used of an acid actalyst, said catalyst consisting essentially of aluminum chloride, ferric chloride, aluminum tris-butoxide, antimony chloride, stanous chloride, cuprous chloride, metallic aluminum powder, metallic antimony, metallic copper or mixtures thereof; the improvement consisting of adding to the reaction mixture from about 0.0001 to 0.5 moles per mole of (A) used of a dioxin inhibitor selected from the group consisting of:

Antimony pentachloride
Chromium dichloride
Chromium powder
Chromium sulfide
Cobalt metal
Gadolinium trichloride
Germanium tetrachloride
Hafnium tetrachloride
Indium chloride
Magnesium turnings
Manganese dichloride
Niobium chloride
Zirconium tetrachloride
Antimony powder
Bismuth trichloride
Chromium metal
Cobalt fluoride
Iridium chloride
Niobium pentachloride
Rhenium pentachloride
Rhodium trichloride
Samarium trichloride
Tantalum chloride
Tin powder
Tungsten hexachloride
Zinc fluoride
Rubidium trichloride
and mixtures thereof.

2. The process of claim 1 wherein a sulfur-containing co-catalyst selected from the group consisting of sulfur, thiophenol, para-chlorothiophenol, para, para'-dichlorophenyl sulfide, sodium hydrosulfide, 2,2'thiobis (4,6-dichlorophenol) benzyl disulfide, dibenzothiophene, benzyldisulfide, diphenyl sulfide, diphenyl disulfide, di-isopentyl sulfide, naphthalenethiols, heptyl sulfide, hexaochlorophenyl sulfide, dicresyl disulfide and dihexadecyl sulfide and thio diphenol is included.

3. The process of claim 1 in which the chlorine in the reaction mixture is sparged through (A).

4. The process of claim 2 in which the chlorine is sparged at a rate of from 300 to 600 g/hr.

5. The process of claim 1 in which the temperature of the reaction mixture is adjusted to a temperature of about 125° C. until the freezing point of the polychlorinated phenols reaches about 115° C. and thereafter maintaining the temperature of the reaction mixture 10° C. above the freezing point of the reaction mixture as the reaction progresses until the freezing point has reached about 180° C.

6. The process of claim 1 in which the polychlorinated phenol produced is pentachlorinated phenol.

7. The process of claim 1 in which the polychlorinated phenol produced is tetrachlorinated phenol.

8. The process of claim 1 in which the inhibitor in the reaction mixture is from 0.0001 to about 0.03 moles per mole of (A) used.

9. The process of claim 1 in which the catalyst is aluminum chloride.

10. The process of claim 1 in which the catalyst is powdered aluminum.

11. The process of claim 1 in which from about 0.05 to about 0.0001 moles per mole of (A) of diphenylsulfide is in the reaction mixture.

12. The polychlorinated phenol produced by the process of claim 1.

13. The polychlorinated phenol of claim 11 which is tetrachlorophenol.

14. The polychlorinated phenol of claim 11 which is pentachlorophenol.

15. A process for producing polychlorinated phenols having reduced amount of chlorinated dioxin formed therein during processing comprising reacting at a temperature of from 10° C. to 190° C. (A) a phenol, which is at least one member selected from a group consisting of phenol and lower chlorophenols and mixtures thereof, and (B) chlorine to form a reaction mixture in the presence of from about 0.005 to about 0.016 moles per mole of (A), used of a catalyst, said catalyst consisting essentially of zirconium tetrachloride or hafnium tetrachloride or mixtures thereof.

* * * * *